United States Patent
Onsager

[11] 3,950,370
[45] Apr. 13, 1976

[54] PROCESS OF DIMERIZATION
[75] Inventor: Olav Torgeir Onsager, Suffern, N.Y.
[73] Assignee: Halcon International, Inc., New York, N.Y.
[22] Filed: Dec. 30, 1974
[21] Appl. No.: 537,296

[52] U.S. Cl. .................................. 260/465.8 D
[51] Int. Cl.² ............................... C07C 120/00
[58] Field of Search ..................... 260/465.8 D

[56] References Cited
UNITED STATES PATENTS

| | | | |
|---|---|---|---|
| 3,644,473 | 2/1972 | Onsager | 260/465.8 D |
| 3,644,474 | 2/1972 | Onsager | 260/465.8 D |
| 3,733,351 | 5/1973 | Watanabe et al. | 260/465.8 D |

Primary Examiner—Joseph P. Brust
Attorney, Agent, or Firm—William C. Long; David Dick; Riggs T. Stewart

[57] ABSTRACT

Acrylonitrile is dimerized by reaction in the presence of a catalyst consisting essentially of (a) at least one metal compound of the formula $M(X)_n$ wherein M is magnesium, chromium or manganese, X is a halide and $n$ is a number equal to the valence of the metal M and (b) at least one nitrogen-containing Lewis Base which is (1) a tertiary monoamine of the formula

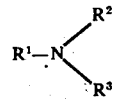

wherein $R^1$, $R^2$, and $R^3$ are the same or different and each is an alkyl, cycloalkyl, benzyl or aryl radical; or (2) a tertiary di- or poly-functional amine which contains at least two Lewis Base nitrogen groups separated from each other by at least one carbon atom, and which are (a) N-disubstituted amino groups wherein each N-substituent is the same or different and is an alkyl, cycloalkyl, benzyl or aryl radical, or (b) N-heterocyclic groups containing three to 20 carbon atoms; or (3) an N-substituted heterocyclic amine containing three to 20 carbon atoms in the heterocyclic ring wherein the N-substituent is an alkyl, cycloalkyl, benzyl or aryl radical.

4 Claims, No Drawings

PROCESS OF DIMERIZATION

This invention relates to the dimerization of nitriles of α,β-unsaturated carboxylic acids and is more particularly concerned with the dimerization of acrylonitrile.

The dimerization of certain α,β-unsaturated carboxylic acid derivatives is a known reaction. For example, acrylonitrile can be dimerized in the presence of a catalyst to produce 2-methylene glutaronitrile (2-MGN). Such dimerization is commonly referred to as "head-to-tail" dimerization since in the dimer the α-carbon atom of one monomer molecule is attached to the β-carbon atom of the other monomer molecule. Various tertiary phosphines, certain types of cyclic tertiary amines having at least one nitrogen atom common to two or three rings, e.g. triethylenediamine (British Pat. No. 1,168,774) and a wide variety of metal carbonyls are known to be suitable for use as catalysts in this reaction. Furthermore, the use of a catalyst system composed of at least one metal halide of the formula $MX_n$ in which M is zinc, aluminum, titanium, vanadium, iron or cobalt, X is a halogen, and $n$ is a number equal to the valence of the metal M and at least one trialkylamine of the formula

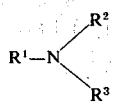

in which $R^1$, $R^2$, and $R^3$ are alkyl groups, is known (British Pat. No. 1,256,392 and U.S. Pat. No. 3,733,351).

The object of the present invention is to provide an improved process for the dimerization of acrylonitrile characterized by the use of a novel catalyst system.

It is a further object of the invention to provide a process of the character indicated which is particularly applicable to the head-to-tail dimerization of acrylonitrile to produce 2-methylene glutaronitrile.

In accordance with the invention, acrylonitrile is dimerized in the presence of a catalyst which consists essentially of (a) at least one metal compound of the formula $M(X)_n$ wherein M is magnesium, chromium or manganese, X is a halide and $n$ is a number equal to the valence of the metal M and (b) at least one nitrogen-containing Lewis Base which is (1) a tertiary monoamine of the formula

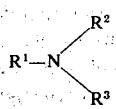

wherein $R^1$, $R^2$, and $R^3$ are the same or different, each an alkyl, cycloalkyl, benzyl or aryl radical; or (2) a tertiary di- or poly-functional amine which contains at least two Lewis Base nitrogen groups separated from each other by at least one carbon atom, and which are (a) N-substituted amino groups wherein each N-substituent is the same or different and is an alkyl, cycloalkyl, benzyl or aryl radical or (b) N-heterocyclic groups containing three to 20 carbon atoms; or (3) an N-substituted heterocyclic amine containing three to 20 carbon atoms in the heterocyclic ring wherein the N-substituent is an alkyl, cycloalkyl, benzyl or aryl radical.

Preferably, the alkyl radicals have one to 20 carbon atoms, the benzyl radicals have seven to 20 carbon atoms and the aryl radicals have six to 20 carbon atoms. In addition, all the radicals, including the heterocyclic rings, may contain non-reactive groups, e.g. nitrile, ether and ester-groups.

The halogen of the (a) component of the catalyst is preferably chlorine, bromine or iodine and typical examples of the (a) component having the formula $M(X)_n$ include $MgBr_2$, $CrCl_2$, $CrBr_3$, $CrI_2$, $MnCl_2$, $MnBr_2$, and $MnI_2$. The preferred metal is chromium.

Typical Lewis Bases suitable for use as the (b) component of the catalyst system of the invention include tertiary monoamines such as trimethylamine, dimethylethylamine, triethylamine, tripropylamine, trihexylamine, methyldiethylamine, 3-diethylaminopropionitrile, dimethylcyclohexylamine, tricyclohexylamine, triisobutylamine, N,N-diethylaniline, N,N-dimethylparatolylamine, N,N-dipropylaniline, N,N-diethylmesitylamine, N,N-dimethylbenzylamine, N,N-diethylbenzylamine, and N,N-dicyclohexylbenzylamine; tertiary di- and poly-amines such as $N,N,N^1,N^1$ tetraethyl-1,6-hexanediamine, N,N-diethylaminomethyl-polystyrene and p-(N,N-diethylamino)-N,N-diethylaniline, methylenedipiperidine; tertiary heterocyclic amines such as N-methylpiperidine, N-ethylpiperidine, N-cyclohexylpiperidine, N-phenylpiperidine, N-benzylpiperidine, N-ethylmorpholine, $N,N^1$-dimethylpiperazine, and N-methylpyrrolidine. The most preferred Lewis Bases are those which are trialkylamines and N-alkyl heterocyclic amines.

It should be understood that the specific (a) and (b) catalyst components identified above are merely representative of suitable compounds and the invention is not limited to these specific compounds but includes like compounds within the generic definition of the (a) and (b) compounds.

The molar ratio between the Lewis base component and the metal salt component can vary widely. In general, the Lewis base/metal salt mole ratio is from 0.1:1 to 25:1, preferably 0.5:1 to 20:1.

The concentration of the metal salt in the reaction zone is suitably selected to give a practical rate of reaction. It has been found that the rate of reaction increases with increasing metal salt concentrations. In general, the metal salt concentration is advantageously from 0.5 to 20 wt. %, the preferred concentration being from 1.0 to 15 wt. %, based on the weight of the liquid-phase reaction mixture.

The catalyst system may be soluble or (at least in part) insoluble in the reaction mixture. A solvent can be used, if desired, but is not necessary for carrying out the dimerization reaction. Preferred solvents are aliphatic or aromatic nitriles, hydrocarbons, especially aromatic hydrocarbons, chlorohydrocarbons, sulfoxides and like organic solvents inert in the dimerization reaction. Examples of preferred solvents include acetonitrile, propionitrile, benzonitrile, hexane, hexadecane, benzene, p-xylene, o-dichlorobenzene, sulfolane and dimethylsulfoxide. The amount of solvent, when used, is suitably 5–80 wt. % of the liquid reaction mixture.

The two catalyst components can be added separately to the reaction zone or they can be premixed before addition. Furthermore, if desired, one or both components can be dissolved in an inert solvent and fed to the reaction zone in the form of a solution.

The pressure and temperature are selected so as to maintain the monomer being dimerized in the liquid phase during the reaction. In general, the temperature is within the range of from 10° to 150°C, the most preferred temperature being from 20° to 100°C. The pressure will, of course, vary with the temperature and typically will be within the range of 0.1 atm. to 100 atm., generally 1 atm. to 10 atm.

If desired, a polymerization inhibitor for the monomer can be used. Such ibhibitors are well known and typical inhibitors include hydroquinone, methylene blue, and p-nitrosodimethylaniline. Very small amounts of inhibitor can be employed, e.g. 5 to 1000 ppm. based on the weight of the monomer.

The process according to the invention can be carried out as a batch process or in continuous fashion. The residence time is selected to give at least 1 wt. % dimer product in the liquid-phase reaction mixture. The concentration of dimer is readily determined by conventional analytical procedures such as gas/liquid chromatography. In general, residence times of less than 10 hours are employed, the preferred residence time being less than 6 hours. In general, a residence time of at least 5 minutes is normally employed.

The effluent is then cooled to room temperature and analyzed by gas/liquid chromatography for 2-methyleneglutaronitrile (product) and unconverted acrylonitrile. The 2-methyleneglutaronitrile yield is determined to be 62.0%. The effluent is flash distilled at reduced pressure. The in hand yield of 2-methyleneglutaronitrile is 51.0% collected as the cut distilling between 130°C and 135°C at 10 mm Hg pressure.

In the following examples, as in this example, the dimer is essentially the only product formed and trimer and acrylonitrile polymer, if detectable at all, are present in very small amounts, demonstrating the highly selective nature of the catalyst in producing dimer.

EXAMPLES 2–12

Using the same general procedure as described in Example 1, a series of experiments are carried out. The feed composition, the conditions of reaction and the data obtained are summarized in Table 1. The 2-methyleneglutaronitrile (2-MGN) yields reported in this table are determined by gas/liquid chromatographic analysis of the effluents and are based on the total amount of acrylonitrile charged to the reactor.

TABLE 1

| EX. NO. | FEED COMPOSITION | | | | CONDITIONS | | 2 MGN |
| | ACRYLONITRILE ML. | LEWIS BASE GRS. | SALT GRS. | SOLVENT ML. | TIME HRS. | TEMP. °C | YIELD % |
| --- | --- | --- | --- | --- | --- | --- | --- |
| 2 | 20 | Triethylamine 2.2 | $CrI_2$ 1.7 | None | 16 | 25 | 53.0 |
| 3 | 25 | Triethylamine 1.45 | $CrBr_3$ 2.0 | None | 16 | 25 | 28.0 |
| 4 | 25 | Triethylamine 2.9 | $CrBr_3$ 2.0 | None | 16 | 25 | 19.0 |
| 5 | 25 | Triethylamine 2.9 | $MnBr_2$ 2.0 | None | 16 | 25 | 23.0 |
| 6 | 25 | Triethylamine 2.9 | $MnI_2$ 2.0 | None | 3 | 60 | 22.5 |
| 7 | 25 | Triethylamine 2.9 | $MgI_2$ 2.0 | None | 3 | 60 | 20.5 |
| 8 | 25 | N,N-diethylaniline 6.0 | $CrCl_2$ 4.0 | Acetonitrile | 3 | 60 | 25.0 |
| 9 | 25 | N,N-dimethylbenzylamine 6.0 | $CrCl_2$ 4.0 | Sulfolane | 2 | 70 | 15.0 |
| 10 | 25 | N,N'-dimethylpiperazine 4.0 | $CrCl_2$ 2.0 | None | 16 | 30 | 56.0 |
| 11 | 25 | N,N,N¹,N¹-tetramethylethylenediamine 4.0 | $MnBr_2$ 2.0 | None | 16 | 30 | 3.7 |
| 12 | 25 | N-methylpiperidine | $MnBr_2$ | None | 16 | 30 | 32.6 |

The dimer product is recovered from the reaction product by conventional means such as distillation or solvent extraction. The catalyst can be reused, if desired, by recycling either or both of the two components, after the dimer and unreacted monomer have been separated from them.

In order to obtain improved rates of reaction the reaction system should be kept substantially anhydrous.

The process of the invention will be more fully understood by reference to the following examples which are given for illustrative purposes only and are not to be interpreted as limitative of the invention.

EXAMPLE 1

Two grams of $MnBr_2$, 25 ml of acrylonitrile (containing 100 ppm hydroquinone) and 4 ml of triethylamine are charged to a 100 ml glass reactor equipped with thermometer, condenser and a magnetic stirrer. The reactor is placed in a constant temperature water bath and the mixture allowed to react for 3 hours at 60°C.

As will be seen from the data provided by the foregoing examples, favorable yields of the dimer product can be obtained with high selectivity and, in addition, an important advantage of the process of the invention is that the components of the reaction mixture can be readily separated from the catalyst.

In the foregoing examples the term "yield" has its usual meaning and can be expressed as follows:

$$\% \text{ yield} = \frac{\text{weight dimer produced}}{\text{weight acrylonitrile charged}} \times 100$$

It will be apparent that various changes and modifications may be made without departing from the invention as defined in the appended claims and it is intended, therefore, that all matter contained in the foregoing description shall be interpreted as illustrative only and not as limitative of the invention.

What is claimed is:

1. A process for the dimerization of acrylonitrile to produce 2-methylene glutaronitrile which comprises reacting said acrylonitrile in the liquid phase at a temperature of 10° to 150°C. in the presence of a catalyst consisting essentially of (a) at least one metal compound of the formula $M(X)_n$ wherein M is magnesium, chromium or manganese, X is a halide and n is a number equal to the valence of the metal M; and (b) at least one nitrogen-containing Lewis Base which is (1) a tertiary monoamine of the formula

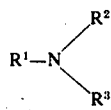

wherein $R^1$, $R^2$, and $R^3$ are the same or different and each is an alkyl, cycloalkyl, benzyl or aryl radical; or (2) a tertiary poly-functional amine which contains at least two Lewis Base nitrogen groups separated from each other by at least one carbon atom, and which are (a) N-disubstituted amino groups wherein each N-substituent is the same or different and is an alkyl, cycloalkyl, benzyl or aryl radical, or (b) N-heterocyclic groups containing three to 20 carbon atoms; or (3) a mono nitrogen-containing N-substituted heterocyclic amine containing three to 20 carbon atoms in the heterocyclic ring wherein the N-substituent is an alkyl, cycloalkyl, benzyl or aryl radical, wherein the Lewis Base/metal compound mole ratio is from 0.1:1 to 25:1, each radical and each heterocyclic group or ring may be unsubstituted or substituted by non-reactive groups, each alkyl radical contains one to 20 carbon atoms and each aryl radical contains six to 20 carbon atoms.

2. A process as defined in claim 1, wherein the metal M is chromium.

3. A process as defined in claim 1, wherein the Lewis Base is a trialkyl amine or an N-alkyl heterocyclic amine.

4. A process as defined in claim 1, wherein the metal M is chromium and the Lewis Base is a trialkyl amine or an N-alkyl heterocyclic amine.

* * * * *